United States Patent
Egmond et al.

(10) Patent No.: US 7,323,612 B2
(45) Date of Patent: Jan. 29, 2008

(54) REMOVAL OF CONDENSABLE COMPOUNDS FROM AN OLEFIN STREAM

(75) Inventors: Cor F. Egmond, Pasadena, TX (US); James R. Lattner, Seabrook, TX (US); Zhong Yi Ding, Wayne, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 163 days.

(21) Appl. No.: 10/929,048

(22) Filed: Aug. 27, 2004

(65) Prior Publication Data

US 2006/0047175 A1 Mar. 2, 2006

(51) Int. Cl.
*C07C 7/00* (2006.01)
*C07C 1/00* (2006.01)

(52) U.S. Cl. ............... 585/809; 585/639; 585/640; 208/48 Q

(58) Field of Classification Search ........... 585/639, 585/640, 809; 208/48 Q
See application file for complete search history.

(56) References Cited

U.S. PATENT DOCUMENTS

| | | | |
|---|---|---|---|
| 4,506,106 A | 3/1985 | Hsia et al. ............... | 585/312 |
| 6,121,504 A | 9/2000 | Kuechler et al. ......... | 585/640 |
| 6,459,009 B1 | 10/2002 | Miller et al. ............. | 585/809 |
| 6,506,954 B1* | 1/2003 | Brown et al. ............. | 585/640 |
| 6,740,791 B2 | 5/2004 | Kuechler et al. ......... | 585/639 |
| 2004/0127763 A1 | 7/2004 | Van Egmond et al. .... | 585/639 |
| 2004/0192982 A1 | 9/2004 | Kuechler et al. ......... | 585/259 |

FOREIGN PATENT DOCUMENTS

WO    WO 02/00579    1/2002

* cited by examiner

*Primary Examiner*—Glenn A. Caldarola
*Assistant Examiner*—In Suk Bullock

(57) ABSTRACT

This invention is directed to a process for condensing and removing condensable compounds from an olefin stream containing light olefin compounds, and recovering the light olefin compounds. The process of the invention is particularly effective in removing water and heavy hydrocarbons, particularly aromatic hydrocarbons, from an olefin stream made from the catalytic conversion of oxygenate, and recovering light olefins such as ethylene, propylene, butylene, or a mixture thereof.

26 Claims, 3 Drawing Sheets

REMOVAL OF CONDENSABLE COMPOUNDS FROM AN OLEFIN STREAM

FIELD OF THE INVENTION

This invention concerns a process for condensing and removing condensable compounds from an olefin stream. In particular, this invention concerns condensing and removing water and heavy hydrocarbons from an olefin stream containing light olefin compounds such as ethylene, propylene and butylene, and recovering the light olefin compounds.

BACKGROUND OF THE INVENTION

Light olefins such as ethylene, propylene and butylene serve as feeds for the production of numerous important chemicals and polymers. Typically, light olefins are produced by cracking petroleum feeds.

An alternative route for manufacturing light olefins is to catalytically convert oxygenates such as methanol to an olefin product. This conversion can be accomplished using a variety of molecular sieve catalysts. Several of these catalysts are highly selective in forming ethylene and propylene. However, a significant amount of water is formed as a natural by-product, and this water must be removed from the desired light olefin product.

U.S. Pat. No. 6,740,791 B2 discloses a process for converting an oxygenate to an olefin product. Water is removed from the olefin product using a quench tower to cool the product and condense the water. The olefin portion of the olefin product is recovered in an overhead stream from the quench tower, and the condensed water fraction is recovered as a bottoms stream. The condensed water fraction is recovered from the quench tower, and sent to a fractionator for separation into further streams.

U.S. Pat. No. 6,459,009 B1 discloses an alternative process for converting an oxygenate to an olefin product. Water is removed from the olefin product using a two-stage quench tower to cool the product and condense the water. The olefin product is passed to a first stage quench tower and contacted with an aqueous stream and a neutralizing agent introduced at the top of the quench tower to provide a hydrocarbon vapor stream and a first stage bottoms stream containing water. The vapor stream is cooled and sent to a second stage tower to further separate light olefins and additional water. A portion of the first stage bottoms stream is withdrawn as a drag stream, and another portion of the first stage bottoms stream is recycled to the first stage tower.

Removing water and other condensable materials from an olefin stream can be problematic. For example, water that is recovered should be relatively low in hydrocarbon components, and the recovered olefin compounds should be relatively free of water. In addition, systems for separating the condensable materials from the light olefin compounds should be low in maintenance and should be easy to operate. There is, therefore, a need to pursue more efficient ways of removing water and other condensable materials from olefin streams, particularly olefin streams high in light olefin content.

SUMMARY OF THE INVENTION

This invention provides a more efficient means of removing water and other condensable materials from olefin streams. The invention is particularly advantageous in recovering olefin produced from oxygenates.

Accordingly, in one aspect of the invention, there is provided a process for removing one or more liquid streams from an olefin stream produced from an oxygenate. In one embodiment, the invention comprises contacting the oxygenate with a molecular sieve catalyst to form an olefin stream. At least a portion of the olefin stream is condensed in a quench vessel, and an olefin vapor stream, a liquid water stream, and a hydrocarbon stream are removed from the vessel. The hydrocarbon stream can be in the liquid or vapor phase.

In one embodiment of the invention, the hydrocarbon stream is removed in substantially the vapor state. Preferably, at least a portion of the hydrocarbon vapor stream is further condensed to form a hydrocarbon layer and a water layer.

In another aspect of the invention, there is provided a process for recovering olefin produced from oxygenate. The process includes a step of contacting an oxygenate with a molecular sieve catalyst to form an olefin stream. At least a portion of the olefin stream is condensed in a vessel to form an olefin vapor stream and a liquid water stream, and the hydrocarbon vapor stream is removed from the vessel.

In one embodiment, the olefin vapor stream contains at least 50 wt % olefin, based on total weight of the olefin vapor stream. Preferably, the stream contains light olefins such as ethylene, propylene and butylene.

In another embodiment of the invention, the separated water layer has a TOC content of not greater than 1,000 ppm. In still another embodiment, the separated hydrocarbon stream contains at least 10 wt % $C_6+$ compounds, based on total weight of the hydrocarbon stream.

The separated hydrocarbon layer preferably has an initial boiling point of not less than 215° F. (102° C.). More preferably, the separated hydrocarbon stream has a final boiling point of not greater than 850° F. (454° C.).

Separate water and hydrocarbon layers can be formed in a vessel in which the olefin stream is condensed. Alternatively, separate water and hydrocarbon layers can be formed in a vessel separate from that in which the olefin stream is condensed.

In one embodiment, the water and hydrocarbon layers are separated using a weir internal to the vessel in which the olefin stream is condensed. Preferably, the condensation is carried out in a quench vessel.

In another embodiment, a quench vessel is used that contains a liquid separation system in a lower portion of the vessel. Preferably, a hydrocarbon draw is positioned in one portion of the quench vessel and a separate liquid water draw is positioned below the hydrocarbon draw.

BRIEF DESCRIPTION OF THE DRAWINGS

Various embodiments of the invention are also described in the accompanying drawings, wherein.

DETAILED DESCRIPTION OF THE INVENTION

Figure 1:
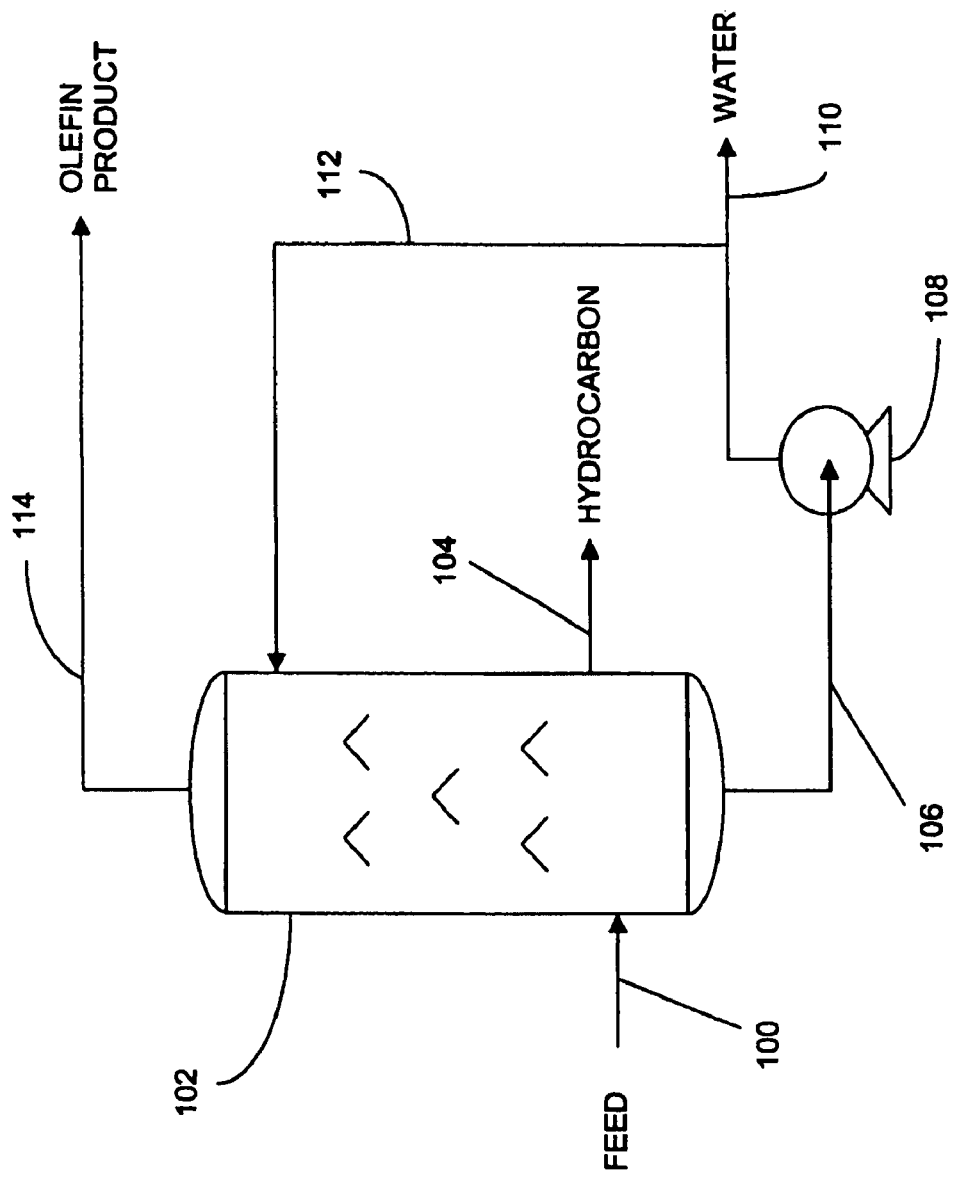
FIG. 1 is a flow diagram of separate hydrocarbon and water streams being removed from a quench vessel.

I. Removal of Hydrocarbon from Condensed Stream

This invention involves the efficient recovery of light olefins such as ethylene, propylene, and butylene. The olefins are preferably produced by the catalytic conversion of oxygenate compounds. This conversion is typically carried out in the vapor phase to produce a vapor phase product.

In the conversion of oxygenates to light olefins, a significant amount of by-products are also typically produced, particularly water. The inventors have found that simple cooling and condensing to separate the water by-product from the desired light olefin product is problematic in that there is a tendency for the condensed stream to contain a significant amount of hydrocarbon, particularly heavy hydrocarbon compounds. When the condensed stream is high in heavy hydrocarbon content, there is not only a significant biological load added to the water removal and recovery system, but there is a tendency for the vessel in which the cooling takes place to be adversely affected by accumulation of the heavy hydrocarbon compounds. In severe cases, an emulsion layer can form, causing further separation problems.

The invention avoids many of the problems associated with condensing the water by-product by removing a separate hydrocarbon stream as a by-product stream. Typically, the separate hydrocarbon stream, which also typically contains at least some water, is formed following cooling and condensing of at least a portion of the olefin stream containing the water by-product. Preferably, the olefin stream is cooled such that a substantial portion of the water contained in the olefin stream is condensed to form a liquid water stream. Condensation is carried out in a vessel, and following condensation, an olefin vapor stream, the liquid water stream and a hydrocarbon stream are removed from the vessel. The olefin vapor stream that is removed from the vessel is preferably a light olefin stream, preferably comprising one or more olefins selected from the group consisting of ethylene, propylene and butylene.

In one embodiment, the hydrocarbon stream, which typically includes at least some water mixed with hydrocarbon, is removed from the vessel in which condensation takes place in the vapor phase. Following removal of the hydrocarbon vapor stream from the vessel, at least a portion of the vapor stream is condensed to from a liquid hydrocarbon layer and a liquid water layer. The separate liquid hydrocarbon and water layers can then be separated from one another as a separate liquid hydrocarbon stream and a separate water stream.

In another embodiment, the hydrocarbon stream is removed from the vessel in which condensation takes place in the liquid phase. Typically, regardless of the phase of the hydrocarbon stream, the hydrocarbon stream can be removed from the vessel as a top layer and a liquid water stream can be removed as a bottom layer, even though the hydrocarbon stream can contain some amount of water. This is generally because the amount of water in the hydrocarbon stream is typically low.

The hydrocarbon stream is preferably removed from the condensation vessel as a separate layer or stream. This allows for removal and recovery of a separate liquid water layer or stream that is low in hydrocarbon content. Such a water stream can be sent directly to a waste treatment system, for example, as it will be low in total organic content (TOC).

II. Oxygenate to Olefins Reaction System

In one embodiment of the invention, an olefin stream is obtained by contacting oxygenate with a molecular sieve catalyst. The oxygenate comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol preferably has from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{10}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, ethanol, dimethyl ether, or a mixture thereof.

Molecular sieves capable of converting an oxygenate to an olefin compound include zeolites as well as non-zeolites, and are of the large, medium or small pore type. Small pore molecular sieves are preferred in one embodiment of this invention, however. As defined herein, small pore molecular sieves have a pore size of less than or equal to about 5.0 angstroms. Generally, suitable catalysts have a pore size ranging from about 3.5 to about 5.0 angstroms, preferably from about 4.0 to about 5.0 angstroms, and most preferably from about 4.3 to about 5.0 angstroms.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One type of olefin forming catalyst capable of producing large quantities of ethylene and propylene is a silicoaluminophosphate (SAPO) molecular sieve. Silicoaluminophosphate molecular sieves are generally classified as being microporous materials having 8, 10, or 12 membered ring structures. These ring structures can have an average pore size ranging from about 3.5 to about 15 angstroms. Preferred are the small pore SAPO molecular sieves having an average pore size of less than or equal to about 5 angstroms, preferably an average pore size ranging from about 3.5 to about 5 angstroms, more preferably from about 3.5 to about 4.2 angstroms. These pore sizes are typical of molecular sieves having 8 membered rings.

According to one embodiment, substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides, which can have an AlPO$_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of MO$_2$, AlO$_2$ and PO$_2$ tetrahedral units. These as manufactured structures (which contain template prior to calcination) can be represented by empirical chemical composition, on an anhydrous basis, as:

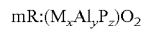

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials, which can be blended with the molecular sieve, can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, and acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference.

Preferred molecular sieves, which can be combined with a silicoaluminophosphate catalyst, include ZSM-5, ZSM-34, erionite, and chabazite.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 angstroms to about 3,000 angstroms, more preferably from about 30 angstroms to about 200 angstroms, most preferably from about 50 angstroms to about 150 angstroms.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

A molecular sieve catalyst particularly useful in making ethylene and propylene is a catalyst, which contains a combination of SAPO-34, and SAPO-18 or ALPO-18 molecular sieve. In a particular embodiment, the molecular sieve is a crystalline intergrowth of SAPO-34, and SAPO-18 or ALPO-18.

To convert oxygenate to olefin, conventional reactor systems can be used, including fixed bed, fluid bed or moving bed systems. Preferred reactors of one embodiment are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to about 1000 $hr^{-1}$, and most preferably in the range of from about 50 $hr^{-1}$ to about 500 $hr^{-1}$. WHSV is defined herein as the weight of oxygenate, and reactive hydrocarbon which may optionally be in the feed, per hour per weight of the molecular sieve in the reactor. Because the catalyst or the feedstock may contain other materials which act as inerts or diluents, the WHSV is calculated on the weight basis of the oxygenate feed, and any reactive hydrocarbon which may be present with the oxygenate feed, and the molecular sieve contained in the reactor.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow with a relatively high content of oxygenated olefin by-products being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least 1 psia (7 kPa), preferably at least about 5 psia (34 kPa). The process is particularly effective at higher total pressures, including a total pressure of at least about 20 psia (138 kPa). Preferably, the total pressure is at least about 25 psia (172 kPa), more preferably at least about 30 psia (207 kPa). For practical design purposes it is desirable to use methanol as the primary oxygenate feed component, and operate the reactor at a pressure of not greater than about 500 psia (3445 kPa), preferably not greater than about 400 psia (2756 kPa), most preferably not greater than about 300 psia (2067 kPa).

Undesirable by-products can be avoided by operating at an appropriate gas superficial velocity. As the gas superficial velocity increases the conversion decreases avoiding undesirable by-products. As used herein, the term, "gas superficial velocity" is defined as the combined volumetric flow rate of vaporized feedstock, which includes diluent when present in the feedstock, as well as conversion products, divided by the cross-sectional area of the reaction zone. Because the oxygenate is converted to a product having significant quantities of ethylene and propylene while flowing through the reaction zone, the gas superficial velocity may vary at different locations within the reaction zone. The degree of variation depends on the total number of moles of gas present and the cross section of a particular location in the reaction zone, temperature, pressure and other relevant reaction parameters.

In one embodiment, the gas superficial velocity is maintained at a rate of greater than 1 meter per second (m/s) at least one point in the reaction zone. In another embodiment, it is desirable that the gas superficial velocity is greater than about 2 m/s at least one point in the reaction zone. More desirably, the gas superficial velocity is greater than about 2.5 m/s at least one point in the reaction zone. Even more desirably, the gas superficial velocity is greater than about 4 m/s at least one point in the reaction zone. Most desirably, the gas superficial velocity is greater than about 8 m/s at least one point in the reaction zone.

According to yet another embodiment of the invention, the gas superficial velocity is maintained relatively constant in the reaction zone such that the gas superficial velocity is maintained at a rate greater than 1 m/s at all points in the reaction zone. It is also desirable that the gas superficial velocity be greater than about 2 m/s at all points in the reaction zone. More desirably, the gas superficial velocity is greater than about 2.5 m/s at all points in the reaction zone. Even more desirably, the gas superficial velocity is greater than about 4 m/s at all points in the reaction zone. Most desirably, the gas superficial velocity is greater than about 8 m/s at all points in the reaction zone.

The amount of ethylene and propylene produced in the oxygenate to olefin process can be increased by reducing the conversion of the oxygenates in the oxygenate to olefins reaction. However, reducing the conversion of feed oxygenates in the oxygenate conversion reaction tends to increase the amount of oxygenated hydrocarbons, particularly including dimethyl ether, that are present in the olefin product. Thus, control of the conversion of feed to the oxygenate reaction process can be important.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

In this invention, weight percent conversion is calculated on a water free basis unless otherwise specified. Weight percent conversion on a water free basis is calculated as: 100×(weight oxygenate fed on a water free basis−weight oxygenated hydrocarbon in the product on a water free basis). The water free basis of oxygenate is calculated by subtracting out the water portion of the oxygenate in the feed and product, and excluding water formed in the product. For example, the weight flow rate of methanol on an oxygenate free basis is calculated by multiplying the weight flow rate of methanol by 14/32 to remove the water component of the methanol. As another example, the rate flow rate of dimethyl ether on an oxygenate free basis is calculated by multiplying the weight flow rate of dimethyl ether by 40/46 to remove the water component of the dimethyl ether. If there is a mixture of oxygenates in the feed or product, trace oxygenates are not included. When methanol and/or dimethyl ether is used as the feed, only methanol and dimethyl ether are used to calculate conversion on a water free basis.

In this invention, selectivity is also calculated on a water free basis unless otherwise specified. Selectivity is calculated as: 100×wt % component/(100−wt % water−wt % methanol−wt % dimethyl ether) when methanol and/or dimethyl ether is used as the feed.

III. Removing Water from the Olefin Product

The oxygenate to olefin process forms a substantial amount of water as a by-product. Much of this water by-product can be removed from the olefin product of the oxygenate to olefin process by cooling the olefin product and condensing at least a portion of the product to form an olefin vapor stream and a condensed, liquid stream, with the condensed stream containing a substantial amount of water. Preferably, the olefin product from the oxygenate to olefin process is cooled to a temperature below the condensation temperature of the condensation temperature of the water vapor in the stream in order to condense the undesirable by-products. More particularly, the temperature of the olefin product stream is cooled to a temperature below the condensation temperature of the oxygenate feed used in the oxygenate to olefin process. In certain embodiments, the olefin product is cooled below the condensation temperature of ethanol, and in certain embodiments below that of methanol.

Upon condensation, a liquid stream is formed that is rich in water by-product. The vapor stream that remains following condensation is rich in olefins, particularly the light olefins (e.g., one or more of ethylene, propylene and butylene).

The olefin vapor stream that is removed following condensation typically contains at least 50 wt % total olefin, based on total weight of the vapor stream. Preferably, the olefin vapor stream that is removed following condensation contains at least 60 wt %, more preferably at least 70 wt %, and most preferably at least 80 wt % total olefin, based on total weight of the vapor stream.

The olefin vapor stream that is removed following condensation is also low in water content. In one embodiment, the olefin vapor stream contains not greater than about 20 wt % water, preferably not greater than about 15 wt % water, more preferably not greater than about 12 wt % water.

In one embodiment, a hydrocarbon stream containing heavy hydrocarbon is also condensed and allowed to settle so as to form a water layer and a hydrocarbon layer. The hydrocarbon layer may contain some water, but will generally be somewhat less dense than the water layer, so there is a tendency to form a hydrocarbon layer above a water layer. The layers can be formed in the same vessel in which the olefin stream was condensed or in a separate vessel. The layers are then separated into respective streams for further processing. Preferably, the separated heavy hydrocarbon layer or stream is rich in $C_6+$ hydrocarbons, with $C_6+$ referring to hydrocarbons having a boiling point of hexene or greater.

The separated water layer or stream is relatively low in total organic content (TOC). Preferably, the water layer has a TOC content of not greater than 1,000 ppm, based on total weight of the separated water stream. Such a stream is substantially low in TOC content, which allows the stream to be sent directly to a waste treatment system without putting undue load on the system. The water layer is formed and separated in a preferred embodiment so that the water layer has a TOC content of not greater than 750 ppm, more preferably not greater than 500 ppm, and most preferably not greater than 250 ppm, based on total weight of the separated water layer.

The separated hydrocarbon layer, which is typically finally separated in the liquid phase, contains a substantial portion of hydrocarbons that have a boiling point higher than that of water. In one embodiment, the separated hydrocarbon layer has an initial boiling point of not less than 215° F. (102° C.). In another embodiment, the separated hydrocarbon layer has an initial boiling point of not less than 230° F. (110° C.), or not less than 250° F. (121° C.), or not less than 275° F. (135° C.), or not less than 300° F. (149° C.). In yet another embodiment, the separated hydrocarbon layer has a final boiling point of not greater than 850° F. (454° C.), preferably not greater than 800° F. (427° C.), and more preferably not greater than 750° F. (399° C.). The initial and final boiling points are preferably determined using ASTM D-86 test procedures.

The separated hydrocarbon layer preferably contains a significant amount of hydrocarbons having a boiling point of hexene or higher ($C_6+$ compounds). In one embodiment, the separated hydrocarbon stream contains at least 10 wt % $C_6+$ compounds, based on total weight of the hydrocarbon stream. In another embodiment, the separated hydrocarbon stream contains at least 20 wt %, 30 wt %, 40 wt %, or 50 wt % $C_6+$ compounds, based on total weight of the separated hydrocarbon stream.

A quench column is one type of equipment that can be used to condense the olefin stream to form the olefin vapor stream and the liquid stream. In a quench column, a quenching fluid is directly contacted with the olefin stream to cool the stream to the desired condensation temperature. Condensation produces the liquid stream, which can also be referred to as a bottoms stream. The light olefin portion of the olefin stream remains a vapor, and exits the quench column as an overhead vapor stream. The overhead vapor stream is rich in light olefin product, and can also contain some oxygenated hydrocarbon by-products as well as some water.

In one embodiment, the quenching fluid is a recycle stream of the condensed liquid stream of the quench column. This stream, which is rich in water, is desirably cooled, e.g., by a heat exchanger, and injected back into the quench column. It is preferred in this embodiment to not inject cooling medium from an outside source into the quench column, although in certain embodiments additional cooling medium such as water from an outside source can be injected.

Following quench, the light olefin product is further processed as desired, and the liquid is further separated into separate water and hydrocarbon streams. The water stream can be sent directly to waste treatment, further processed or used in a cooling system or other water re-use dispositions. The hydrocarbon stream can be incinerated to make steam or processed further into other liquid fuel dispositions.

In one embodiment, a quench column is used that contains a liquid separation system in a lower portion of the column. The separation system acts to separate liquid hydrocarbon and liquid water into separate liquid layers, one layer on top of the other.

In another embodiment of the invention, the quench column includes a liquid hydrocarbon draw that is positioned in one portion of the column and a separate liquid water draw that is positioned below the liquid hydrocarbon draw. In another embodiment, a weir is included in the liquid separation system and is used to assist in separating the liquid hydrocarbon layer or layers from the liquid water layer.

In one particular embodiment of the invention, the olefin product stream that is recovered from the quench column is further processed by compression, preferably multi-staged compression. Two, three, four or more stages can be used, with two or three stages being preferred. The compressed stream is then sent to a distillation system and the olefins further separated. Preferably, an ethylene stream containing at least 50 wt %, more preferably at least 75 wt %, and most preferably at least 90 wt % ethylene, based on total weight of the recovered ethylene stream, is recovered. In another embodiment, a propylene stream containing at least 50 wt %, more preferably at least 75 wt %, and most preferably at least 90 wt % propylene, based on total weight of the recovered propylene stream, is recovered.

In another embodiment of the invention, the olefin stream recovered from the quench is compressed to a pressure that is greater than that at which the oxygenate to olefin reaction process is carried out. Preferably, the olefin stream is compressed to a pressure of at least about 30 psia (207 kPa), more preferably at least about 50 psia (345 kPa), most preferably at least about 100 psia (689 kPa). High pressure ranges are particularly preferred, with the upper limit being a practical one based on cost of design and ease of operation. Practical high pressure limits are generally considered to be up to about 5,000 psia (34,450 kPa), with lower limits of about 1,000 psia (6,895 kPa), about 750 psia (5171 kPa), and about 500 psia (3447 kPa) being increasingly preferred. Following compression to the desired pressure, the olefin stream is separated into two or more olefin streams. For example, the compressed olefin stream can be sent to one or more distillation columns and separate olefin streams, such as ethylene and propylene streams, can be recovered.

IV. Examples

Various non-limiting embodiments of the invention are shown in the attached Figures. According to the embodiment shown in FIG. 1, olefin feed containing light olefin, various hydrocarbon by-products and water by-product is sent through a line 100 to a quench column 102. In the quench column 102, at least a portion of the olefin feed is condensed to form an olefin vapor stream and a liquid water stream.

The liquid water stream is removed from the quench column 102 by way of a line 106, and sent to a pump 108. From the pump 108, a portion of the water stream is sent to a waste treatment system through a line 110 and a portion is sent back to the quench column 102 through a line 112 to act as a cooling medium. Light olefin product is removed from the quench column 102 by way of a line 114.

A hydrocarbon stream is removed from the quench column 102 by way of a line 104 as a side draw. The hydrocarbon stream can be either in the liquid phase or the vapor phase.

Figure 2:
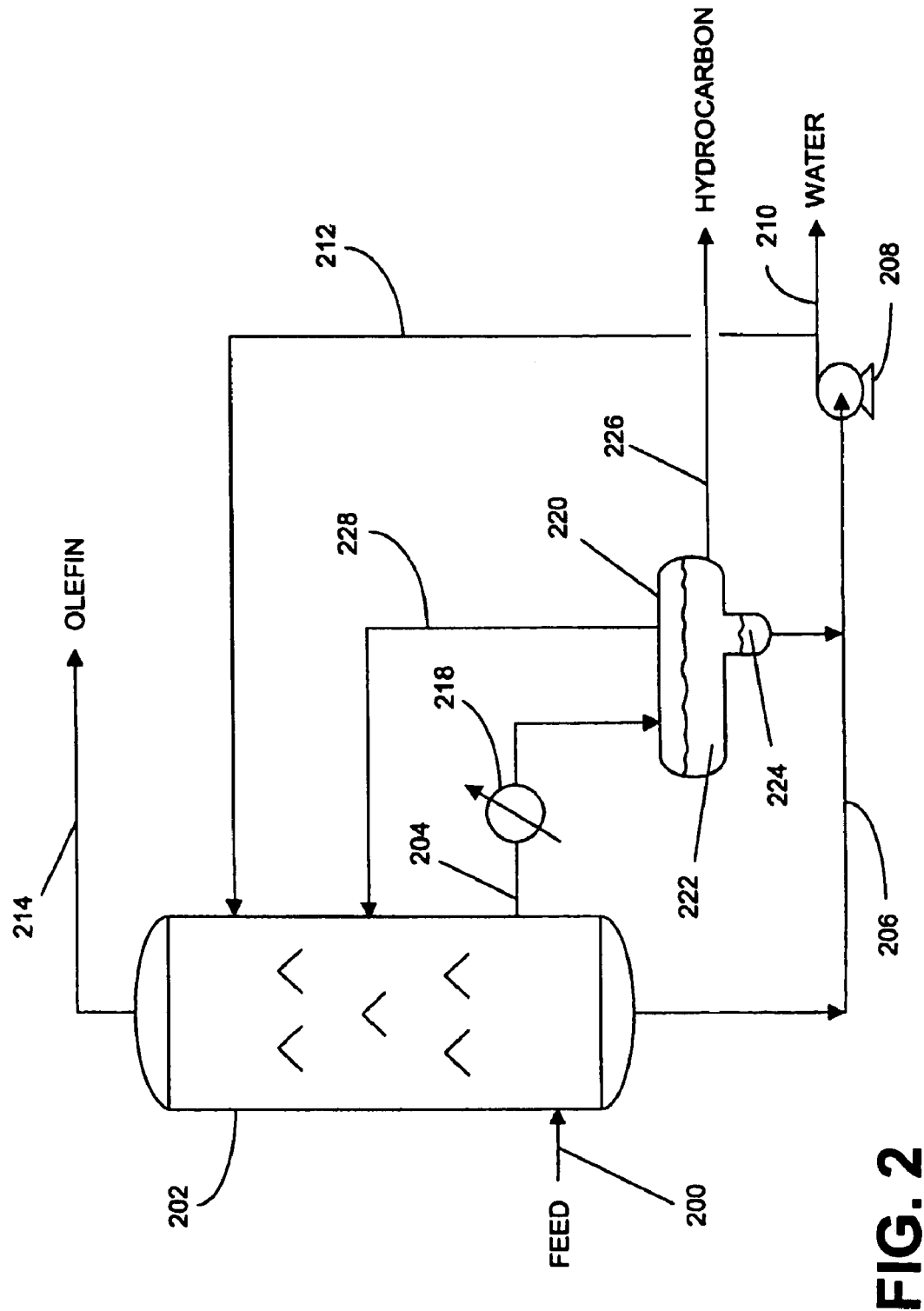
FIG. 2 is a flow diagram of separate hydrocarbon and water streams being removed from a settling vessel following a quench vessel.

In the embodiment shown in FIG. 2, olefin feed containing light olefin, various hydrocarbon by-products and water by-product is sent through a line 200 to a quench column 202. In the quench column 202, a portion of the olefin feed is condensed to form an olefin vapor stream and a liquid water stream. The liquid water stream is removed from the quench column 202 by way of a line 206 and sent to a pump 208. From the pump 208, a portion of the water stream is sent to a waste treatment system through a line 210 and a portion is sent back to the quench column 202 through a line 212 to act as a cooling medium. Light olefin product is removed from the quench column 202 by way of a line 214.

A hydrocarbon stream is removed from the quench column 202 by way of a line 204. The hydrocarbon stream flowing through the line 204 is at least partially in the vapor state. The stream is further cooled by way of a heat exchanger 218 and sent to a settler 220. In the settler 220, the hydrocarbon stream is allowed to sit for an additional period of time so that a hydrocarbon rich layer 222 separates from a water layer 224.

The hydrocarbon layer 222 is removed from the settler 220 by way of a line 226. The water layer 224 is removed and combined with the water stream flowing through line 206. In addition, a vapor stream containing light olefin entrapped in the hydrocarbon stream is sent to the quench column 202 by way of a line 228 for further processing and removal.

Figure 3:
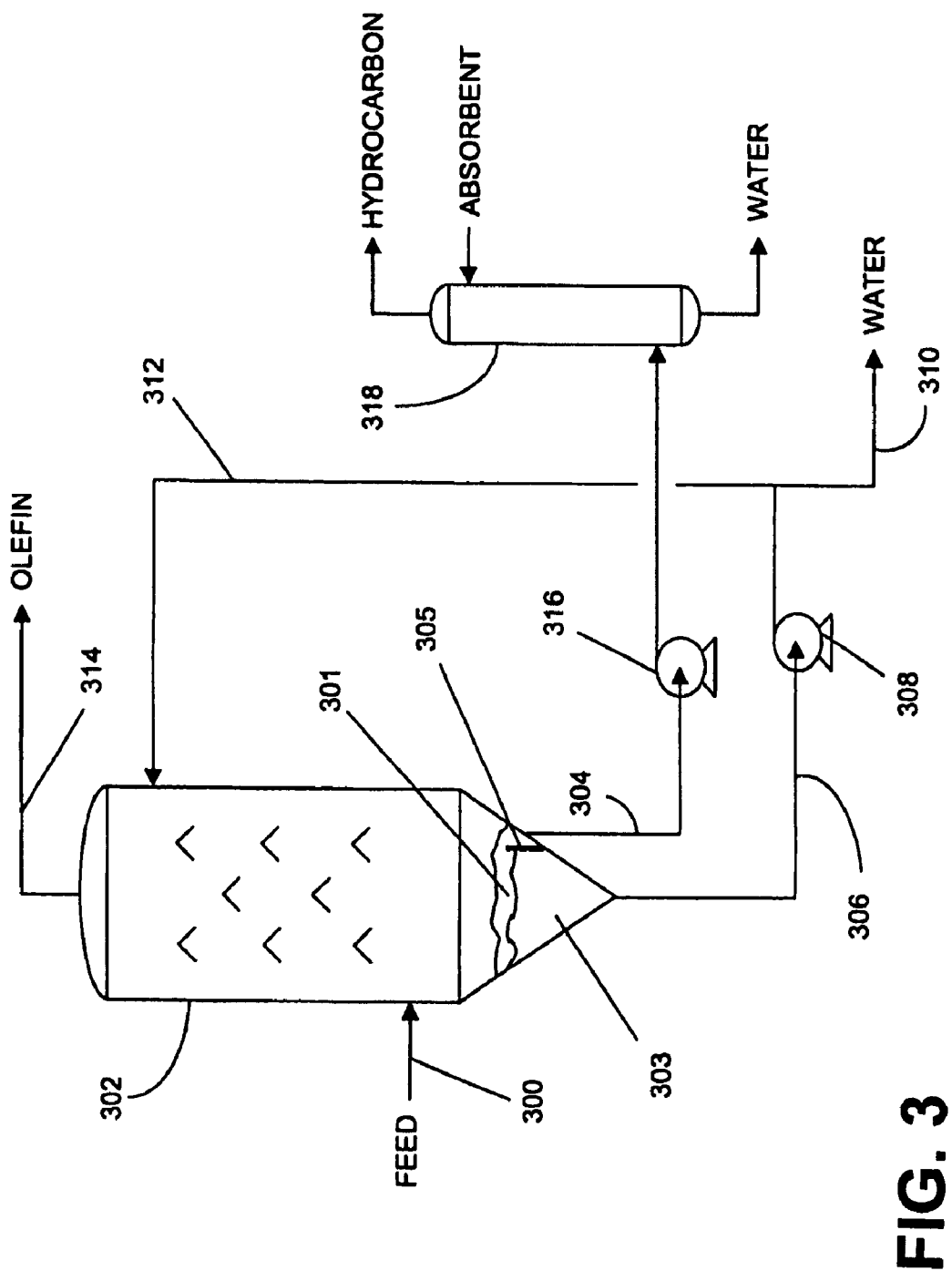
FIG. 3 is a flow diagram of a quench vessel having an internal weir to aid in separating the hydrocarbon and water layers.

In the embodiment shown in FIG. 3, olefin feed containing light olefin, various hydrocarbon by-products and water by-product is sent through a line 300 to a quench column 302. In the quench column 302, a portion of the olefin feed is condensed to form an olefin vapor stream and a liquid stream. The liquid stream settles out in quench column 302 as a separate hydrocarbon layer 301 and a separate water layer 303. A hydrocarbon stream is removed from the quench column 302 by way of a line 304, using a weir 305 to aid in keeping the hydrocarbon layer 301 and the water layer 303 separate.

A water stream is removed from the quench column 302 by way of a line 306 and sent to a pump 308. From the pump 308, a portion of the water stream is sent to a waste treatment stream through a line 310 and a portion is sent back to the quench column 302 through a line 312 to act as a cooling medium. Light olefin product is removed from the quench column 302 by way of a line 314.

The hydrocarbon stream that is sent through the line 304 is sent to an absorber column 318 by way of a pump 316 to remove water that may be entrained in the hydrocarbon. An absorbent such as water or any water compatible water absorbent is added to the absorber column to assist in separating the entrained water from the hydrocarbon. A hydrocarbon stream is removed from an overhead of the absorber column 318 and a water stream, including absorbent, is removed as a bottoms stream.

Having now fully described this invention, it will be appreciated by those skilled in the art that the invention can be performed within a wide range of parameters within what is claimed, without departing from the spirit and scope of the invention.

We claim:

1. A process for removing one or more liquid streams from an olefin stream produced from an oxygenate, comprising:
   a) contacting the oxygenate with a molecular sieve catalyst to form an olefin stream comprising olefin product and hydrocarbon by-product;
   b) condensing a portion of the olefin stream in a quench vessel; and
   c) removing from the quench vessel a separate olefin product vapor stream, a separate liquid water stream, and a separate by-product hydrocarbon stream, wherein a portion of the separate liquid water stream is sent to the quench vessel to act as cooling medium to condense the portion of the olefin stream in the quench vessel.

2. The process of claim 1, wherein the by-product hydrocarbon stream is in the liquid or vapor state.

3. The process of claim 2, wherein the by-product hydrocarbon stream is in the vapor state.

4. The process of claim 3, wherein at least a portion of the by-product hydrocarbon vapor stream is separately condensed to form a hydrocarbon layer and a water layer.

5. The process of claim 1, wherein the quench vessel contains a liquid separation system in a lower portion of the vessel.

6. The process of claim 1, wherein a by-product hydrocarbon draw is positioned in one portion of the quench vessel and a separate liquid water draw is positioned below the by-product hydrocarbon draw.

7. The process of claim 1, wherein a weir is positioned in the quench vessel to assist in separating a liquid by-product hydrocarbon layer or layers from a liquid water layer.

8. The process of claim 1, wherein the product olefin vapor stream contains at least 50 wt % olefin, based on total weight of the olefin vapor stream.

9. The process of claim 1, wherein the liquid water stream removed from the quench vessel has a TOC content of not greater than 1,000 ppm.

10. The process of claim 1, wherein the by-product hydrocarbon stream removed from the quench vessel has an initial boiling point of not less than 215° F. (102° C.).

11. The process of claim 9, wherein the by-product hydrocarbon stream has a final boiling point of not greater than 850° F. (454° C.).

12. The process of claim 1, wherein the by-product hydrocarbon stream contains at least 10 wt % $C_6$+ compounds, based on total weight of the by-product hydrocarbon stream.

13. A process for recovering olefin produced from oxygenate, comprising:
   a) contacting an oxygenate with a molecular sieve catalyst to form an olefin stream comprising olefin product, water, and hydrocarbon by-product;
   b) condensing at least a portion of the olefin stream in a quench vessel to form within the vessel an olefin product vapor, hydrocarbon by-product, and liquid water with a portion of the water being sent back to the quench vessel to act as a cooling medium; and
   c) removing from the quench vessel the olefin product vapor as a separate olefin product vapor stream, the liquid water as a separate liquid water stream, and the hydrocarbon by-product as a separate by-product hydrocarbon stream, wherein the portion of the water that is sent back to the quench vessel is sent back as a separate liquid water stream to act as the cooling medium.

14. The process of claim 13, wherein the olefin product vapor stream contains at least 50 wt % olefin, based on total weight of the olefin product vapor stream.

15. The process of claim 13, wherein at least a portion of the by-product hydrocarbon stream is condensed following removal from the vessel to form a liquid by-product hydrocarbon layer and a liquid water layer.

16. The process of claim 15, wherein the liquid water layer is separated from the liquid by-product hydrocarbon layer.

17. The process of claim 16, wherein the separated by-product hydrocarbon layer has an initial boiling point of not less than 215° F. (102° C.).

18. The process of claim 17, wherein the separated by-product hydrocarbon stream has a final boiling point of not greater than 850° F. (454° C.).

19. The process of claim 16, wherein the separated water layer has a TOC content of not greater than 1,000 ppm.

20. The process of claim 16, wherein the separated by-product hydrocarbon layer contains at least 10 wt % $C_6$+ compounds, based on total weight of the by-product hydrocarbon layer.

21. The process of claim 15, wherein the water and by-product hydrocarbon layers are formed in a vessel in which the olefin stream is condensed.

22. The process of claim 15, wherein the water and by-product hydrocarbon layers are formed in a vessel separate from that in which the olefin stream is condensed.

23. The process of claim 15, wherein the water and by-product hydrocarbon layers are separated using a weir internal to the vessel in which the olefin stream is condensed.

24. The process of claim 13, wherein the quench vessel contains a liquid separation system in a lower portion of the vessel.

25. The process of claim 13, wherein the liquid water stream is removed from the vessel at a location below that from which the by-product hydrocarbon vapor stream is removed.

26. The process of claim 1, wherein the molecular sieve catalyst comprises SAPO-34, SAPO-18, ALPO-18, or mixtures thereof.

* * * * *